(12) United States Patent
Schnabel et al.

(10) Patent No.: US 8,198,214 B2
(45) Date of Patent: *Jun. 12, 2012

(54) SOLID FORMULATION

(75) Inventors: Gerhard Schnabel, Elsenfeld (DE); Hans-Peter Krause, Hofheim (DE)

(73) Assignee: Bayer CropScience AG, Monheim (DE)

( * ) Notice: Subject to any disclaimer, the term of this patent is extended or adjusted under 35 U.S.C. 154(b) by 680 days.

This patent is subject to a terminal disclaimer.

(21) Appl. No.: 11/522,286

(22) Filed: Sep. 15, 2006

(65) Prior Publication Data

US 2007/0066487 A1 Mar. 22, 2007

(30) Foreign Application Priority Data

Sep. 16, 2005 (EP) .................... 05020219

(51) Int. Cl.
*A01N 25/26* (2006.01)
*A01N 43/653* (2006.01)

(52) U.S. Cl. ...................... 504/100; 504/273

(58) Field of Classification Search .............. None
See application file for complete search history.

(56) References Cited

U.S. PATENT DOCUMENTS

| | | | |
|---|---|---|---|
| 4,933,000 A | 6/1990 | Somlo | |
| 5,534,486 A | 7/1996 | Müller et al. | |
| 5,543,385 A | 8/1996 | Röchling et al. | |
| 5,650,375 A | 7/1997 | Hacker et al. | |
| 6,242,382 B1 | 6/2001 | Bratz et al. | |
| 6,482,772 B1 | 11/2002 | Bratz et al. | |
| 6,559,098 B1 | 5/2003 | Bratz et al. | |
| 6,650,375 B1 | 11/2003 | Maeda | |
| 7,138,360 B2 * | 11/2006 | Jager et al. | 504/211 |
| 2005/0113254 A1 | 5/2005 | Ziemer et al. | |

FOREIGN PATENT DOCUMENTS

| | | |
|---|---|---|
| EP | 0 367 887 | 5/1990 |
| EP | 0 413 267 | 2/1991 |
| EP | 0 507 171 A1 | 10/1992 |
| EP | 0 764 404 | 3/1997 |
| EP | 1 277 405 | 1/2003 |
| JP | 62-084004 | 4/1987 |
| WO | WO-93/13658 | 7/1993 |
| WO | WO-98/33383 | 8/1998 |
| WO | WO-98/34482 | 8/1998 |
| WO | WO-98/42192 | 10/1998 |
| WO | WO-02/17718 | 3/2002 |
| WO | WO-02/17718 * | 5/2002 |

OTHER PUBLICATIONS

Hay, J. V., "Chemistry of Sulfonylurea Herbicides", Pesticide Science 29:3 (1990), pp. 247-261.
English language abstract from Esp@cenet database of JP62084004.

* cited by examiner

*Primary Examiner* — Alton Pryor
(74) *Attorney, Agent, or Firm* — Connolly Bove Lodge & Hutz LLP

(57) ABSTRACT

The present invention relates to a solid formulation comprising
a) one or more sulfonamides,
b) one or more surfactants, and
c) at least 2% by weight of water.
The solid formulation is suitable for the field of crop protection.

15 Claims, No Drawings

SOLID FORMULATION

The present invention relates to the field of the plant protection composition formulations. In particular, the invention relates to solid formulations, preferably in the form of granules, which comprise herbicidal active substances from the group of the sulfonamides, in particular the phenylsulfonamides and heteroarylsulfonamides.

Active substances for plant protection are generally not employed in their pure form. Depending on the field of application and the route of application, and on physical, chemical and biological parameters, the active substance is employed as a mixture with customary adjuvants and additives in the form of an active substance formulation. The combinations with further active substances for widening the spectrum of action and/or for protecting the crop plants (for example by safeners, antidotes) are also known.

Formulations of active substances for plant protection should generally have a high chemical and physical stability, good applicability and user friendliness, and a broad biological activity combined with high selectivity.

Herbicidal active substances from the group of the sulfonamides, such as sulfonylureas, are generally highly reactive chemically and are prone to chemical degradation, for example by hydrolysis.

One possibility of formulating chemically unstable active substances is the preparation of solid formulations. Thus formulations of active substances from the group of the sulfonylureas are known in the form of powders, granules and tablets (for example in EP 764404, WO 9834482, WO 9313658).

However, the preparation of a spray liquor from sulfonamide-comprising solid formulations, in particular from granules, can prove difficult, for example as the result of clogged screens and washing-in locks, in particular with the use of liquid fertilizers. As a result, certain tank mixes can either be not prepared at all, or specific mixing procedures must be adhered to strictly to be able to prepare the tank mixes in the first place and to avoid application problems.

A further potential problem of solid formulations consists in the fact that they tend to develop dust. This problem can be exacerbated when sulfonamide-comprising solid formulations have a small particle size and a high sulfonamide content, in particular as the result of electrostatic charging.

The object of the present invention consisted in providing sulfonamide-comprising solid formulations which avoid the abovementioned problems.

Surprisingly, it has now been found that this object is achieved by the sulfonamide-comprising solid formulations of the present invention.

The present invention thus relates to solid agrochemical formulations comprising
a) one or more sulfonamides,
b) one or more surfactants, and
c) at least 2% by weight of water.

In addition, the solid formulation according to the invention can, if appropriate, also comprise as further components:
d) one or more agrochemical active substances other than a), and
e) customary adjuvants and additives other than b).

A solid formulation within the meaning of the present invention is understood as meaning, for example, granules, powders, dusts (cf. Spray Drying Handbook; 3rd Ed.; K. Masters (1979); George Yodwin Limited, London; John Wiley & Sons, New York), in particular wettable powders (WP), water-soluble powders (SP), dusts (DP), granules for broadcasting and soil application, granules (GR) in the form of micro-granules, spray granules, coated granules and adsorption granules, water-dispersible granules (WG), water-soluble granules (SG). These individual formulation types are known in principle and are described, including their preparation, for example, in: Winnacker-Küchler, "Chemische Technologie" [Chemical Technology], Volume 7, C. Hauser Verlag Munich, 4$^{th}$ Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London. The formulation auxiliaries required, such as inert materials, surfactants, solvents and further additives, are also known and are described, for example, in Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie", Volume 7, C. Hauser Verlag Munich, 4$^{th}$ Ed. 1986.

Based on these formulations, it is also possible to prepare combinations with other agrochemical active substances other than the herbicidally active sulfonamides a) such as insecticides, acaricides, herbicides, fungicides, safeners, fertilizers such as ammonium sulfate, ammonium hydrogen sulfate, ammonium nitrate, urea and their mixtures, and/or growth regulators, for example in the form of a readymix or a tank mix.

Wettable powders are products which are uniformly dispersible in water and which, besides the active substance, may also comprise diluents or inert materials and various ionic and/or nonionic surfactants (wetters, dispersants), for example polyoxyethylated alkylphenols, polyoxethylated fatty alcohols, polyoxethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltauride. To prepare the wettable powders, the herbicidal active substances a), surfactants b) and water c) are ground finely, for example in customary apparatuses such as hammer mills, blower mills and air-jet mills, and mixed with the formulation auxiliaries, either simultaneously or subsequently.

Dusts are obtained by grinding the active substance a) with finely divided solid materials, for example talc, natural clays such as kaolin, bentonite and pyrophyllite, or diatomaceous earth, and with surfactants b) and water c).

Granules can be prepared either by spraying the active substance a), surfactants b) and/or other adjuvants/further agrochemical active substances onto adsorptive, granulated inert material or by applying active ingredient concentrates to the surface of carriers such as sand, kaolinites or granulated inert material with the aid of adhesives, for example polyvinyl alcohol, sodium polyacrylate or else mineral oils. Suitable active substances a), surfactants b), water c) and/or other adjuvants may also be granulated in the manner conventionally used for the production of fertilizer granules, if desired in a mixture with fertilizers.

As a rule, water-dispersible granules are prepared from the components a), b), c) and if appropriate d) and e) by conventional processes such as spray drying, fluidized-bed granulation, disk granulation, mixing with high-speed mixers or extrusion.

Regarding the production of disk granules, fluidized-bed granules, extruder granules and spray granules, see, for example, the methods in "Spray-Drying Handbook" 3rd Ed. 1979, G. Goodwin Ltd., London; J. E. Browning, "Agglomeration", Chemical and Engineering 1967, page 147 et seq.; "Perry's Chemical Engineer's Handbook", 5th Ed., McGraw-Hill, New York 1973, pp. 8-57.

For further details on the formulation of crop protection products, see, for example, G. C. Klingman, "Weed Control as a Science", John Wiley and Sons, Inc., New York, 1961, pages 81-96 and J. D. Freyer, S. A. Evans, "Weed Control Handbook", 5th Ed., Blackwell Scientific Publications, Oxford, 1968, pages 101-103.

The solid formulations according to the invention preferably comprise 25 to 97.9% by weight, by preference 50 to 95% by weight, especially preferably 60 to 95% by weight, of one or more sulfonamides a).

In wettable powders, the sulfonamide concentration preferably amounts to 50 to 95% by weight, the remainder to 100% by weight consists of components b), c) and optionally d) and e). Formulations in the form of dusts preferably comprise 50 to 80% by weight of sulfonamide. In the case of granules, the sulfonamide content is preferably 50 to 95% by weight, preferably 60 to 90% by weight.

In addition, the solid formulations according to the invention may comprise, if appropriate, customary adjuvants and additives such as tackifiers, wetters, dispersants, emulsifiers, penetrants, preservatives, antifreeze agents, solvents, fillers, carriers, colorants, antifoams, and adjuvants such as mineral or vegetable oils and their derivatives, evaporation inhibitors, pH regulators or viscosity regulators.

Preferred solid formulations are granules which are prepared by known methods, such as by spray drying, for example in a fluidized bed, extrusion, Shugi granulation or disk granulation. Especially preferred are water-soluble granules (SG), in particular those prepared by spray drying.

Suitable as component a) are herbicidally active sulfonamides, preferably from the group of the phenylsulfonamides, heteroarylsulfonamides and the other sulfonamides such as amidosulfuron. Suitable as phenylsulfonamides a) are, for example, compounds from the group of the phenylsulfonylaminocarbonyl-triazolinones or the phenylsulfonylureas, preferably from the group of the phenylsulfonylureas. The term phenylsulfonylureas is also understood as including those sulfonylureas in which the phenyl group is bonded to the sulfone group ($SO_2$) via a spacer such as $CH_2$, O or NH. Examples of phenylsulfonylaminocarbonyl-triazolinones are flucarbazone or propoxycarbazone and/or their salts. The sulfonamides a) are commercially available and/or can be prepared by known processes as they are described for example in EP-A-7687, EP-A-30138, U.S. Pat. No. 5,057,144 and U.S. Pat. No. 5,534,486.

Suitable as phenylsulfonamides are, for example, phenylsulfonamides of the general formula (I) and/or their salts,

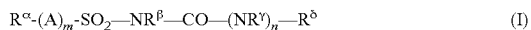

$$R^\alpha\text{-}(A)_m\text{-}SO_2\text{---}NR^\beta\text{---}CO\text{---}(NR^\gamma)_n\text{---}R^\delta \qquad (I)$$

in which
$R^\alpha$ is a phenyl radical which is unsubstituted or substituted, the phenyl radical including substituents having 1-30 carbon atoms, preferably 1-20 carbon atoms,
$R^\beta$ is a hydrogen atom or a hydrocarbon radical which is unsubstituted or substituted and including substituents has 1-10 carbon atoms, for example unsubstituted or substituted $C_1$-$C_6$-alkyl, preferably a hydrogen atom or methyl,
$R^\gamma$ is a hydrogen atom or a hydrocarbon radical which is unsubstituted or substituted and including substituents has 1-10 carbon atoms, for example unsubstituted or substituted $C_1$-$C_6$-alkyl, preferably a hydrogen atom or methyl,
A is $CH_2$, O or NH, preferably O,
m is zero or 1,
n is zero or 1, preferably 1, and
$R^\delta$ is a heterocyclic radical such as a pyrimidinyl radical, a triazinyl radical or a triazolinone radical.

Preferred phenylsulfonamides are phenylsulfonylureas, for example phenylsulfonylureas of the general formula (II) and/or their salts,

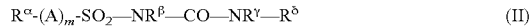

$$R^\alpha\text{-}(A)_m\text{-}SO_2\text{---}NR^\beta\text{---}CO\text{---}NR^\gamma\text{---}R^\delta \qquad (II)$$

in which
$R^\alpha$ is a phenyl radical which is unsubstituted or substituted, the phenyl radical including substituents having 1-30 carbon atoms, preferably 1-20 carbon atoms,
$R^\beta$ is a hydrogen atom or a hydrocarbon radical which is unsubstituted or substituted and including substituents has 1-10 carbon atoms, for example unsubstituted or substituted $C_1$-$C_6$-alkyl, preferably a hydrogen atom or methyl,
$R^\gamma$ is a hydrogen atom or a hydrocarbon radical which is unsubstituted or substituted and including substituents has 1-10 carbon atoms, for example unsubstituted or substituted $C_1$-$C_6$-alkyl, preferably a hydrogen atom or methyl,
A is $CH_2$, O or NH, preferably O,
m is zero or 1, and
$R^\delta$ is a heterocyclic radical such as a pyrimidinyl radical or a triazinyl radical.

Preferred are phenylsulfonylureas of the formula (III) and/or their salts,

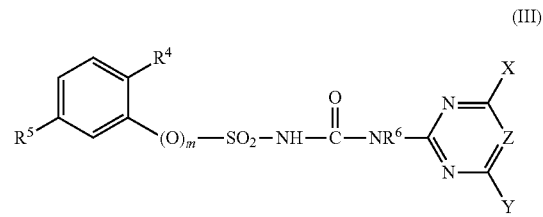

(III)

in which
$R^4$ is $C_1$-$C_4$-alkoxy, preferably $C_2$-$C_4$-alkoxy, or CO—$R^a$, where $R^a$ is OH, $C_1$-$C_4$-alkoxy or $NR^bR^c$, where $R^b$ and $R^c$ independently of one another are identical or different and are H or $C_1$-$C_4$-alkyl,
$R^5$ is halogen, preferably iodine, or $(A)_n$-$NR^dR^e$ where n is zero or 1, A is a group CR'R" where R' and R" independently of one another are identical or different and are H or $C_1$-$C_4$-alkyl, $R^d$ is H or $C_1$-$C_4$-alkyl and $R^e$ is an acyl radical such as formyl or $C_1$-$C_4$-alkylsulfonyl, and $R^5$ in the event that $R^4$ is $C_1$-$C_4$-alkoxy, preferably $C_2$-$C_4$-alkoxy, may also be H,
$R^6$ is H or $C_1$-$C_4$-alkyl,
m is zero or 1,
X and Y independently of one another are identical or different and are halogen or NR'R" where R' and R" are identical or different and are H or $C_1$-$C_4$-alkyl, or $C_1$-$C_6$-alkyl, $C_1$-$C_6$-alkoxy, $C_1$-$C_6$-alkylthio, $C_3$-$C_6$-cycloalkyl, $C_2$-$C_6$-alkenyl, $C_2$-$C_6$-alkynyl, $C_3$-$C_6$-alkenyloxy or $C_3$-$C_6$-alkynyloxy, where each of the eight last-mentioned radicals is unsubstituted or substituted by one or more radicals selected from the group consisting of halogen, $C_1$-$C_4$-alkoxy and $C_1$-$C_4$-alkylthio, preferably $C_1$-$C_4$-alkyl or $C_1$-$C_4$-alkoxy, and
Z is CH or N.

Especially preferred are phenylsulfonylureas of the general formula (III) and/or their salts, in which
a) $R^4$ is CO—($C_1$-$C_4$-alkoxy), $R^5$ is halogen, preferably iodine, or $R^5$ is $CH_2$—$NHR^e$, where $R^e$ is an acyl radical, preferably $C_1$-$C_4$-alkylsulfonyl, and m is zero,
b) $R^4$ is CO—N($C_1$-$C_4$-alkyl)$_2$, $R^5$ is $NHR^e$ where $R^e$ is an acyl radical, preferably formyl, and m is zero, or
c) $R^4$ is $C_2$-$C_4$-alkoxy, $R^5$ is H and m is 1.

Typical phenylsulfonylureas are, inter alia, the compounds listed hereinbelow and their salts, such as the sodium salts: bensulfuron-methyl, chlorimuron-ethyl, chlorsulfuron, cinosulfuron, cyclosulfamuron, ethametsulfuron-methyl, ethoxysulfuron and its sodium salt, metsulfuron-methyl, oxasulfuron, primisulfuron-methyl, prosulfuron, sulfometuron-methyl, triasulfuron, tribenuron-methyl, triflusulfuron-methyl, tritosulfuron, iodosulfuron-methyl and its sodium salt (WO 92/13845), mesosulfuron-methyl and its sodium salt (Agrow No. 347, 3 Mar. 2000, page 22 (PJB Publications Ltd. 2000)) and foramsulfuron and its sodium salt (Agrow No. 338, 15 Oct. 1999, page 26 (PJB Publications Ltd. 1999)).

Especially preferred phenylsulfonamides are: iodosulfuron-methyl (A1.1) and its salts such as the sodium salt (A1.2), mesosulfuron-methyl (A2.1) and its salts such as the sodium salt (A2.2), foramsulfuron (A3.1) and its salts such as the sodium salt (A3.2), flucarbazone (A4.1) and its salts such as the sodium salt (A4.2), propoxycarbazone (A5.1) and its salts such as the sodium salt (A5.2) and ethoxysulfuron (A6.1) and its salts such as the sodium salts (A6.2), metsulfuron-methyl (A7.1) and its salts such as the sodium salt (A7.2), tribenuron-methyl (A8.1) and its salts such as the sodium salt (A8.2), chlorsulfuron (A9.1) and its salts such as the sodium salt (A9.2).

The abovementioned active substances are known for example from "The Pesticide Manual", 12th edition (2000), The British Crop Protection Council, or from the references cited after the individual active substances.

Heteroarylsulfonamides a) which are suitable are, for example, compounds from the group of heteroarylsulfonylaminocarbonyltriazolinones or of the heteroarylsulfonylureas, preferably from the group of the heteroarylsulfonylureas. The term heteroarylsulfonylureas is also understood as including those sulfonylureas in which the heteroaryl group is bonded to the sulfone group (SO$_2$) via a spacer such as CH$_2$, O or NH.

Suitable heteroarylsulfonamides are, for example, sulfonamides of the general formula (IV) and/or their salts,

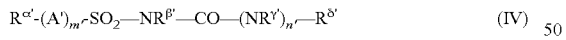  (IV)

in which
$R^{\alpha'}$ a is a heteroaryl radical which is unsubstituted or substituted, the heteroaryl radical including substituents having 1-30 carbon atoms, preferably 1-20 carbon atoms,
$R^{\beta'}$ is a hydrogen atom or a hydrocarbon radical which is unsubstituted or substituted and including substituents has 1-10 carbon atoms, for example unsubstituted or substituted $C_1$-$C_6$-alkyl, preferably a hydrogen atom or methyl,
$R^{\gamma'}$ is a hydrogen atom or a hydrocarbon radical which is unsubstituted or substituted and including substituents has 1-10 carbon atoms, for example unsubstituted or substituted $C_1$-$C_6$-alkyl, preferably a hydrogen atom or methyl,
A' is CH$_2$, O or NH, preferably O,
m' is zero or 1,
n' is zero or 1, preferably 1, and
$R^{\delta'}$ is a heterocyclic radical such as a pyrimidinyl radical, a triazinyl radical or a triazolinone radical.

Preferred heteroarylsulfonamides are heteroarylsulfonylureas, for example sulfonylureas of the general formula (V) and/or their salts,

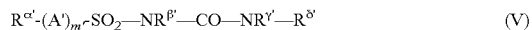  (V)

in which
$R^{\alpha'}$ is a heteroaryl radical which is unsubstituted or substituted, the heteroaryl radical including substituents having 1-30 carbon atoms, preferably 1-20 carbon atoms,
$R^{\beta'}$ is a hydrogen atom or a hydrocarbon radical which is unsubstituted or substituted and including substituents has 1-10 carbon atoms, for example unsubstituted or substituted $C_1$-$C_6$-alkyl, preferably a hydrogen atom or methyl,
$R^{\gamma'}$ is a hydrogen atom or a hydrocarbon radical which is unsubstituted or substituted and including substituents has 1-10 carbon atoms, for example unsubstituted or substituted $C_1$-$C_6$-alkyl, preferably a hydrogen atom or methyl,
A' is CH$_2$, O or NH, preferably O,
m' is zero or 1
$R^{\delta'}$ is a heterocyclic radical such as a pyrimidinyl radical or a triazinyl radical.

Especially preferred are heteroarylsulfonamides of the formula (VI) hereinbelow,

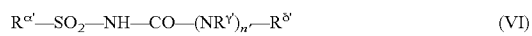  (VI)

in which
$R^{\alpha'}$ is a substituted heteroaryl radical, such as substituted pyridyl, thienyl, pyrazolyl or imidazolyl,
$R^{\gamma'}$ is H, ($C_1$-$C_3$)alkyl, optionally substituted by halogen (F, C, Br, I) or (halo)alkoxy ($C_1$-$C_3$), preferably H or methyl,
for n' is 1, $R^{\delta'}$ is a pyrimidinyl radical or a triazinyl radical, preferably

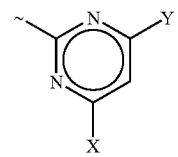

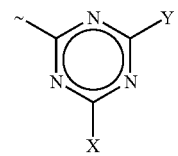

and for n' is zero, $R^{\delta'}$ is triazolinone radical, preferably

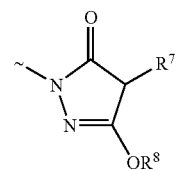

$R^7$ is ($C_1$-$C_{10}$)alkyl which is optionally substituted by halogen (F, Cl, Br, I) or ($C_1$-$C_3$)haloalkyl,
$R^8$ ($C_1$-$C_{10}$)alkyl which is optionally substituted by halogen (F, Cl, Br, I) or ($C_1$-$C_3$)haloalkyl,
X and Y independently of one another are identical or different and are halogen or NR'R", where R' and R" are identical or different and are H or $C_1$-$C_4$-alkyl, or $C_1$-$C_6$-alkyl, $C_1$-$C_6$-alkoxy, $C_1$-$C_6$-alkylthio, $C_3$-$C_6$-cycloalkyl, $C_2$-$C_6$-alkenyl, $C_2$-$C_6$-alkynyl, $C_3$-$C_6$-alkenyloxy or $C_3$-$C_6$-alkynyloxy, where each of the eight last-mentioned radicals is unsubstituted or substituted by one or more radicals selected from the group consisting of halogen, $C_1$-$C_4$-alkoxy and $C_1$-$C_4$-alkylthio, preferably $C_1$-$C_4$-alkyl or $C_1$-$C_4$-alkoxy.

Especially preferably, $R^{\alpha'}$ is

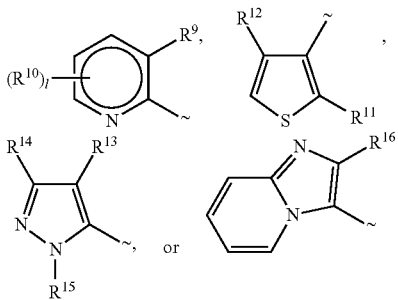

where $R^9$ is $(C_1$-$C_6)$alkyl, $(C_1$-$C_6)$alkoxy, $(C_2$-$C_6)$alkenyloxy, $(C_2$-$C_6)$alkynyloxy, $(C_1$-$C_6)$alkylsulfonyl, $(C_1$-$C_6)$alkylcarbonyl, $(C_1$-$C_6)$alkoxycarbonyl, $(C_2$-$C_6)$alkenyloxycarbonyl, $(C_2$-$C_6)$alkynyloxycarbonyl, CONR'R", $(C_1$-$C_6)$haloalkyl, $(C_1$-$C_6)$haloalkoxy, $(C_2$-$C_6)$haloalkenyloxy, $(C_2$-$C_6)$haloalkynyloxy, $(C_1$-$C_6)$haloalkylsulfonyl, $(C_1$-$C_6)$haloalkylcarbonyl, $(C_1$-$C_6)$haloalkoxycarbonyl, $(C_2$-$C_6)$haloalkenyloxycarbonyl, $(C_2$-$C_6)$halo-alkynyloxycarbonyl, $R^{10}$ is H, $(C_1$-$C_3)$alkyl, $(C_1$-$C_3)$alkoxy, $(C_1$-$C_3)$haloalkyl, $(C_1$-$C_3)$haloalkoxy or halogen (F, Cl, Br, I), l is zero or 1, $R^{11}$ is $(C_1$-$C_6)$alkyl, $(C_1$-$C_6)$alkoxy, $(C_2$-$C_6)$alkenyloxy, $(C_2$-$C_6)$alkynyloxy, $(C_1$-$C_6)$alkylsulfonyl, $(C_1$-$C_6)$alkylcarbonyl, $(C_1$-$C_6)$alkoxycarbonyl, $(C_2$-$C_6)$alkenyloxycarbonyl, $(C_2$-$C_6)$alkynyloxycarbonyl, $(C_1$-$C_6)$haloalkyl, $(C_1$-$C_6)$haloalkoxy, $(C_2$-$C_6)$haloalkenyloxy, $(C_2$-$C_6)$haloalkynyloxy, $(C_1$-$C_6)$haloalkylsulfonyl, $(C_1$-$C_6)$haloalkylcarbonyl, $(C_1$-$C_6)$haloalkoxy-carbonyl, $(C_2$-$C_6)$haloalkenyloxycarbonyl, $(C_2$-$C_6)$haloalkynyloxycarbonyl, CONR'R", $R^{12}$ is halogen (F, Cl, Br, I), $(C_1$-$C_6)$alkyl, $(C_1$-$C_6)$alkoxy, $(C_1$-$C_6)$alkylsulfonyl, $(C_1$-$C_6)$alkoxycarbonyl, $(C_2$-$C_6)$alkenyloxycarbonyl, $(C_2$-$C_6)$alkynyloxy-carbonyl, $(C_1$-$C_6)$haloalkyl, $(C_1$-$C_6)$haloalkoxy, $(C_1$-$C_6)$haloalkylsulfonyl, $(C_1$-$C_6)$haloalkoxycarbonyl, $(C_2$-$C_6)$haloalkenyloxycarbonyl, $(C_2$-$C_6)$haloalkynyloxycarbonyl, $R^{13}$ is $(C_1$-$C_6)$alkoxycarbonyl, $(C_2$-$C_6)$alkenyloxycarbonyl, $(C_2$-$C_6)$alkynyloxy-carbonyl, $(C_1$-$C_6)$alkyl, $(C_1$-$C_6)$alkoxy, $(C_1$-$C_6)$alkylsulfonyl, $(C_1$-$C_6)$halo-alkoxycarbonyl, $(C_2$-$C_6)$haloalkenyloxycarbonyl, $(C_2$-$C_6)$haloalkynyloxy-carbonyl, $(C_1$-$C_6)$haloalkyl, $(C_1$-$C_6)$haloalkoxy, $(C_1$-$C_6)$haloalkylsulfonyl, halogen (F, Cl, Br, I), CONR'R", or $R^{13}$ is a heterocylic ring which can be saturated, unsaturated or aromatic and preferably comprises 4-6 ring atoms and one or more hetero atoms selected from the group consisting of N, O, S, and which can optionally be substituted by one or more substituents, preferably selected from the group consisting of $(C_1$-$C_3)$alkyl, $(C_1$-$C_3)$alkoxy, $(C_1$-$C_3)$haloalkyl, $(C_1$-$C_3)$haloalkoxy or halogen, especially preferably

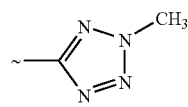

$R^{14}$ is H, halogen (F, C, Br, I), $(C_1$-$C_6)$alkyl, $(C_1$-$C_6)$haloalkyl, $R^{15}$ is H, $(C_1$-$C_6)$alkyl, $(C_1$-$C_6)$haloalkyl, $R^{16}$ is $(C_1$-$C_6)$alkyl, $(C_1$-$C_6)$alkoxy, $(C_2$-$C_6)$alkenyloxy, $(C_2$-$C_6)$alkynyloxy, $(C_1$-$C_6)$alkylsulfonyl, $(C_1$-$C_6)$alkylcarbonyl, $(C_1$-$C_6)$alkoxycarbonyl, $(C_2$-$C_6)$alkenyloxycarbonyl, $(C_2$-$C_6)$alkynyloxycarbonyl, $(C_1$-$C_6)$haloalkyl, $(C_1$-$C_6)$haloalkoxy, $(C_2$-$C_6)$haloalkenyloxy, $(C_2$-$C_6)$haloalkynyloxy, $(C_1$-$C_6)$haloalkylsulfonyl, $(C_1$-$C_6)$haloalkylcarbonyl, $(C_1$-$C_6)$haloalkoxy-carbonyl, $(C_2$-$C_6)$haloalkenyloxycarbonyl, $(C_2$-$C_6)$haloalkynyloxycarbonyl, CONR'R", in particular $SO_2$-ethyl, and R' and R" independently of one another are H, $(C_1$-$C_6)$alkyl, $(C_1$-$C_6)$haloalkyl, $(C_2$-$C_6)$alkenyl, $(C_2$-$C_6)$haloalkenyl, $(C_2$-$C_6)$alkynyl, $(C_2$-$C_6)$haloalkynyl, or NR'R" forms a heterocylic ring which can be saturated, unsaturated or aromatic and preferably comprises 4-6 ring atoms and one or more hetero atoms selected from the group consisting of N, O, S and which can optionally be substituted by one or more substituents, preferably selected from the group consisting of $(C_1$-$C_3)$alkyl, $(C_1$-$C_3)$alkoxy, $(C_1$-$C_3)$haloalkyl, $(C_1$-$C_3)$haloalkoxy or halogen.

Especially preferred heteroarylsulfonylureas are, for example, nicosulfuron (A10.1) and its salts such as the sodium salt (A10.2), rimsulfuron (A11.1) and its salts such as the sodium salt (A11.2), thifensulfuron-methyl (A12.1) and its salts such as the sodium salt (A12.2), pyrazosulfuron-ethyl (A13.1) and its salts such as the sodium salt (A13.2), flupyrsulfuron-methyl (A14.1) and its salts such as the sodium salt (A14.2), sulfosulfuron (A15.1) and its salts such as the sodium salt (A15.2), trifloxysulfuron (A16.1) and its salts such as the sodium salt (A16.2), azimsulfuron (A17.1) and its salts such as the sodium salt (A17.2), flazasulfuron (A18.1) and its salts such as the sodium salt (A18.2) and flucetosulfuron (1-[3-[[[[(4,6-dimethoxy-2-pyrimidinyl)amino]carbonyl]amino]sulfonyl]-2-pyridinyl]-2-fluoropropylmethoxyacetate, (A19.1)) and its salts such as the sodium salt (A19.2).

Especially preferred heteroarylsulfonylaminocarbonyltriazolinones are the compounds of the formula (VII) which are mentioned hereinbelow, which are known, for example, from WO 03/026427.

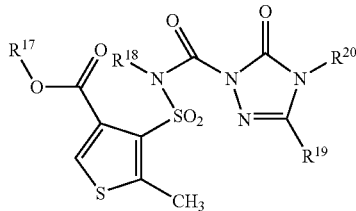

(VII)

| Compound No. | $R^{17}$ | $R^{18}$ | $R^{19}$ | $R^{20}$ |
|---|---|---|---|---|
| A20.1 | $CH_3$ | H | $OC_2H_5$ | $CH_3$ |
| A20.2 | $CH_3$ | Na | $OC_2H_5$ | $CH_3$ |
| A21.1 | $CH_3$ | H | $OCH_3$ | $CH_3$ |
| A21.2 | $CH_3$ | Na | $OCH_3$ | $CH_3$ |

-continued

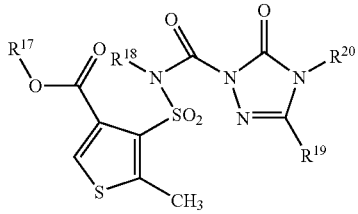

(VII)

| Compound No. | $R^{17}$ | $R^{18}$ | $R^{19}$ | $R^{20}$ |
|---|---|---|---|---|
| A22.1 | $CH_3$ | H | $OC_3H_7$-n | $CH_3$ |
| A22.2 | $CH_3$ | Na | $OC_3H_7$-n | $CH_3$ |
| A23.1 | $CH_3$ | H | $OC_3H_7$-i | $CH_3$ |
| A23.2 | $CH_3$ | Na | $OC_3H_7$-i | $CH_3$ |
| A24.1 | $CH_3$ | H | $OCH_3$ | cyclopropyl |
| A24.2 | $CH_3$ | Na | $OCH_3$ | cyclopropyl |
| A25.1 | $CH_3$ | H | $OC_2H_5$ | cyclopropyl |
| A25.2 | $CH_3$ | Na | $OC_2H_5$ | cyclopropyl |
| A26.1 | $CH_3$ | H | $OC_3H_7$-n | cyclopropyl |
| A26.2 | $CH_3$ | Na | $OC_3H_7$-n | cyclopropyl |
| A27.1 | $CH_3$ | H | $OC_3H_7$-i | cyclopropyl |
| A27.2 | $CH_3$ | Na | $OC_3H_7$-i | cyclopropyl |
| A28.1 | $CH_3$ | H | cyclopropyl | cyclopropyl |
| A28.2 | $CH_3$ | Na | cyclopropyl | cyclopropyl |
| A29.1 | $CH_3$ | H | $CH_3$ | $CH_3$ |
| A29.2 | $CH_3$ | Na | $CH_3$ | $CH_3$ |
| A30.1 | $CH_3$ | H | $C_2H_5$ | $CH_3$ |
| A30.2 | $CH_3$ | Na | $C_2H_5$ | $CH_3$ |
| A31.1 | $CH_3$ | H | $SCH_3$ | $CH_3$ |
| A31.2 | $CH_3$ | Na | $SCH_3$ | $CH_3$ |
| A32.1 | $CH_3$ | H | $OCH_3$ | $CH_3$ |
| A32.2 | $CH_3$ | Na | $OCH_3$ | $CH_3$ |
| A33.1 | $CH_3$ | H | $CH_2OCH_3$ | cyclopropyl |
| A33.2 | $CH_3$ | Na | $CH_2OCH_3$ | cyclopropyl |
| A34.1 | $CH_3$ | H | $OC_2H_5$ | $CH_3$ |
| A34.2 | $CH_3$ | Na | $OC_2H_5$ | $CH_3$ |
| A35.1 | $CH_3$ | H | $OCH_3$ | cyclopropyl |
| A35.2 | $CH_3$ | Na | $OCH_3$ | cyclopropyl |
| A36.1 | $CH_3$ | H | $C_2H_5$ | $OC_2H_5$ |
| A36.2 | $CH_3$ | Na | $C_2H_5$ | $OC_2H_5$ |
| A37.1 | $CH_3$ | H | $C_2H_5$ | cyclopropyl |
| A37.2 | $CH_3$ | Na | $C_2H_5$ | cyclopropyl |

Very especially preferred sulfoamides a) are phenylsulfonylaminocarbonyl-triazolinones, in particular propoxycarbazone (A5.1) and its salts such as the sodium salt (A5.2).

The abovementioned active substances are known, for example, from "The Pesticide Manual", 12th edition (2000) (PM) and 13th edition (2003), The British Crop Protection Council or from the references mentioned after the individual active substances.

Within the meaning of the present invention, the sulfonamides a), which are present as components in the solid formulations according to the invention, are always understood as meaning all application forms such as acids, esters, salts and isomers such as stereoisomers and optical isomers. Thus, the neutral compounds are always to be understood as including their salts with inorganic and/or organic counterions. Thus, sulfonamides can, for example, form salts in which the hydrogen of the —$SO_2$—NH-group is replaced by an agriculturally suitable cation. These salts are, for example, metal salts, in particular alkali metal salts or alkaline earth metal salts, in particular sodium and potassium salts, or else ammonium salts or salts with organic amines. Equally, salt formation can be accomplished by an addition reaction between an acid and basic groups, such as, for example, amino and alkylamino. Acids which are suitable for this purpose are strong inorganic and organic acids, for example HCl, HBr, $H_2SO_4$ or $HNO_3$. Preferred esters are the alkyl esters, in particular the $C_1$-$C_{10}$-alkyl esters, such as methyl ester.

If the present description uses the term acyl radical, this is taken to mean the radical of an organic acid which formally arises by elimination of an OH group from the organic acid, for example the radical of a carboxylic acid and radicals of acids derived therefrom such as thiocarboxylic acid, optionally N-substituted iminocarboxylic acids, or the radicals of carbonic monoesters, optionally N-substituted carbamic acids, sulfonic acids, sulfinic acids, phosphonic acids or phosphinic acids.

An acyl radical is preferably formyl or acyl selected from the group consisting of CO—$R^Z$, CS—$R^Z$, CO—$OR^Z$, CS—$OR^Z$, CS—$SR^Z$, $SOR^Z$ or $SO_2R^Z$, where $R^Z$ is in each case a $C_1$-$C_{10}$-hydrocarbon radical such as $C_1$-$C_{10}$-alkyl or $C_6$-$C_{10}$-aryl, which hydrocarbon radical is unsubstituted or substituted, for example by one or more substituents selected from the group consisting of halogen, such as F, Cl, Br, I, alkoxy, haloalkoxy, hydroxyl, amino, nitro, cyano or alkylthio, or $R^Z$ is aminocarbonyl, or aminosulfonyl, the two last-mentioned radicals being unsubstituted, N-monosubstituted or N,N-disubstituted, for example by substituents selected from the group consisting of alkyl or aryl.

Acyl is, for example, formyl, haloalkylcarbonyl, alkylcarbonyl such as ($C_1$-$C_4$)alkylcarbonyl, phenylcarbonyl, it being possible for the phenyl ring to be substituted, or alkyloxycarbonyl, such as ($C_1$-$C_4$) alkyloxycarbonyl, phenyloxy-carbonyl, benzyloxycarbonyl, alkylsulfonyl, such as ($C_1$-$C_4$) alkylsulfonyl, alkylsulfinyl, such as $C_1$-$C_4$(alkylsulfinyl), N-alkyl-1-iminoalkyl, such as N—($C_1$-$C_4$)-1-imino-($C_1$-$C_4$)alkyl and other radicals of organic acids.

A hydrocarbon radical means a straight-chain, branched or cyclic and saturated or unsaturated aliphatic or aromatic hydrocarbon radical, for example alkyl, alkenyl, alkynyl, cycloalkyl, cycloalkenyl or aryl. A hydrocarbon radical preferably has 1 to 40 carbon atoms, by preference 1 to 30 carbon atoms; especially preferably, a hydrocarbon radical is alkyl, alkenyl or alkynyl, each of which has up to 12 carbon atoms, or cycloalkyl having 3, 4, 5, 6 or 7 ring atoms, or phenyl.

Aryl is a mono-, bi- or polycyclic aromatic system, for example phenyl, naphthyl, tetrahydronaphthyl, indenyl, indanyl, pentalenyl, fluorenyl and the like, preferably phenyl.

A heterocyclic radical or ring (heterocyclyl) can be saturated, unsaturated or heteroaromatic and unsubstituted or substituted; by preference, it contains one or more hetero atoms in the ring, by preference selected from the group consisting of N, O and S; it is by preference an aliphatic heterocyclyl radical having 3 to 7 ring atoms or a heteroaromatic radical having 5 or 6 ring atoms and contains 1, 2 or 3 hetero atoms. The heterocyclic radical can be, for example, a heteroaromatic radical or ring (heteroaryl) such as, for example, a mono-, bi- or polycyclic aromatic system in which at least 1 ring contains one or more hetero atoms, for example pyridyl, pyrimidinyl, pyridazinyl, pyrazinyl, triazinyl, thienyl, thiazolyl, oxazolyl, furyl, pyrrolyl, pyrazolyl and imidazolyl, or is a partially or fully hydrogenated radical such as oxiranyl, oxetanyl, pyrrolidyl, piperidyl, piperazinyl, triazolyl, dioxolanyl, morpholinyl, tetrahydrofuryl. Pyrimidinyl and triazinyl are preferred. Suitable substituents for a substituted heterocyclic radical are the substituents given further below, and additionally also oxo. The oxo group can also be present on those hetero ring atoms which can exist in various oxidation numbers, for example in the case of N and S.

Substituted radicals, such as substituted hydrocarbon radicals, for example substituted alkyl, alkenyl, alkynyl, aryl, phenyl and benzyl, or substituted heterocyclyl or heteroaryl, are, for example, a substituted radical which is derived from the unsubstituted skeleton, the substituents being, for example, one or more, preferably 1, 2 or 3, radicals selected from the group consisting of halogen, alkoxy, haloalkoxy, alkylthio, hydroxyl, amino, nitro, carboxyl, cyano, azido, alkoxycarbonyl, alkylcarbonyl, formyl, carbamoyl, mono- and dialkylaminocarbonyl, substituted amino such as acylamino, mono- and dialkylamino, and alkylsulfinyl, haloalkylsulfinyl, alkylsulfonyl, haloalkylsulfonyl and, in the case of cyclic radicals, also alkyl and haloalkyl, and unsaturated aliphatic radicals which correspond to the abovementioned saturated hydrocarbon-containing radicals, such as alkenyl, alkynyl, alkenyloxy, alkynyloxy and the like. In the case of radicals with carbon atoms, those having 1 to 4 carbon atoms, in particular 1 or 2 carbon atoms, are preferred. Preferred are, as a rule, substituents selected from the group consisting of halogen, for example fluorine and chlorine, ($C_1$-$C_4$)alkyl, preferably methyl or ethyl, ($C_1$-$C_4$)haloalkyl, preferably trifluoromethyl, ($C_1$-$C_4$)alkoxy, preferably methoxy or ethoxy, ($C_1$-$C_4$)haloalkoxy, nitro and cyano. Especially preferred in this context are the substituents methyl, methoxy and chlorine.

Optionally substituted phenyl is preferably phenyl which is unsubstituted or mono- or polysubstituted, preferably up to trisubstituted, by identical or different radicals, preferably selected from the group consisting of halogen, ($C_1$-$C_4$)alkyl, ($C_1$-$C_4$)alkoxy, ($C_1$-$C_4$)halogenalkyl, ($C_1$-$C_4$)halogenalkoxy and nitro, for example o-, m- and p-tolyl, 2-, 3- and 4-chlorophenyl, 2-, 3- and 4-trifluoro- and -trichlorophenyl, 2,4-, 3,5-, 2,5- and 2,3-dichlorophenyl, o-, m- and p-methoxyphenyl.

Cycloalkyl means a carbocyclic, saturated ring system, preferably having 3-6 carbon atoms, for example cyclopropyl, cyclobutyl, cyclopentyl or cyclohexyl.

The hydrocarbon-comprising radicals such as alkyl, alkoxy, haloalkyl, haloalkoxy, alkylamino and alkylthio and the corresponding unsaturated and/or substituted radicals can be in each case straight-chain or branched in the carbon skeleton. Unless otherwise specified, the lower carbon skeletons, for example those having 1 to 6 carbon atoms or, in the case of the unsaturated groups, 2 to 6 carbon atoms, are preferred for these radicals. Alkyl radicals, also in the composite meanings such as alkoxy, haloalkyl and the like, are, for example, methyl, ethyl, n- or i-propyl, n-, i-, t- or 2-butyl, pentyls, hexyls, such as n-hexyl, i-hexyl and 1,3-dimethylbutyl, heptyls, such as n-heptyl, 1-methylhexyl and 1,4-dimethylpentyl; alkenyl and alkynyl radicals have the meanings of the possible unsaturated radicals which correspond to the alkyl radicals; alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; alkynyl is, for example, propargyl, but-2-yn-1-yl, but-3-yn-1-yl, 1-methylbut-3-yn-1-yl.

Halogen is, for example, fluorine, chlorine, bromine or iodine. Haloalkyl, -alkenyl and -alkynyl are alkyl, alkenyl or alkynyl, respectively, which are partially or fully substituted by halogen, preferably by fluorine, chlorine and/or bromine, in particular by fluorine or chlorine, for example $CF_3$, $CHF_2$, $CH_2F$, $CF_3CF_2$, $CH_2FCHCl$, $CCl_3$, $CHCl_2$, $CH_2CH_2Cl$; haloalkoxy is, for example, $OCF_3$, $OCHF_2$, $OCH_2F$, $CF_3CF_2O$, $OCH_2CF_3$ and $OCH_2CH_2Cl$; this also applies analogously to haloalkenyl and other halogen-substituted radicals.

The herbicidal active substances a) from the series of the sulfonamides are preferably present in the solid formulations according to the invention in amounts of from 25 to 97.9% by weight, by preference 50 to 95% by weight, especially preferably from 60 to 95% by weight, very especially preferably from 60 to 80% by weight, with the indication "% by weight" here and in all of the description, unless otherwise defined, relating to the relative weight of the component in question based on the total weight of the formulation.

The compounds which are suitable as surfactants b) are known from the literature, for example from McCutcheon's, Emulsifiers & Detergents 1994, Vol. 1: North American Edition and Vol. 2, International Edition; McCutcheon Division, Glen Rock N.J., USA and also from "Surfactants in Consumer Products", J. Falbe, Springer-Verlag Berlin, 1987. Especially suitable as surfactants b) are wetters, emulsifiers and dispersants.

A wetter is preferably selected from the group of the substance classes alkyl sulfates, alkylsulfonates, sulfates and phosphates of alcohols which optionally comprise alkylaryl groups, or alkylarylsulfonates, fat-acylated N-alkyltaurides, alpha-olefinsulfonic acid, alkylated aromatic sulfonic acids, mono- and dialkylsulfosuccinic acid, the salts of all these abovementioned substances, and the alkylpolyglycosides, the ethers and esters between optionally alkylated polyalkylene oxides and aliphatic or aromatic alcohols or carboxylic acids, furthermore the reaction products of aliphatic or aromatic mono- or polyamines with alkylene oxides.

Especially preferred are the mono- and disulfonic acids of naphthalene with one or two straight-chain or branched alkyl groups (such as, for example, di-tert-butyl-naphthylsulfonic acid sodium), with the sodium salts of mono- or dialkylnaphthalene-sulfonic acids being especially preferred, for example from BASF (Nekal® BX), Nufarm (Galoryl® MT 804), Akzo Nobel (Morwet® EFW).

Examples of suitable emulsifiers and dispersants are nonionic emulsifiers and dispersants, for example:
1) polyalkoxylated, preferably polyethoxylated, saturated or unsaturated aliphatic alcohols,
   a) having 8 to 24 carbon atoms in the alkyl radical, which is derived from the corresponding fatty acids or from petrochemical products, and
   b) having 1 to 100, preferably 2 to 50, ethylene oxide units (EO), the free hydroxyl group optionally being alkoxylated,
   c) which are commercially available as, for example, the Genapol®X and Genapol®O series (Clariant), the Crovol®M series (Croda) or the Lutensol® series (BASF),
2) polyalkoxylated, preferably polyethoxylated, arylalkylphenols, such as, for example 2,4,6-tris(1-phenylethyl) phenol (tristyrylphenol) with a mean degree of ethoxylation of between 10 and 80, preferably 16 to 40, such as, for example, Soprophor®BSU (Rhodia) or HOE S 3474 (Clariant),
3) polyalkoxylated, preferably polyethoxylated alkylphenols with one or more alkyl radicals, such as, for example, nonylphenol or tri-sec-butylphenol, and a degree of ethoxylation of between 2 and 40, preferably 4 to 15, such as, for example, the Arkopal®N series or Sapogenat®T series (Clariant),
4) polyalkoxylated, preferably polyethoxylated hydroxy-fatty acids or glycerides containing hydroxyl-fatty acids glycerides, such as, for example, ricininne or castor oil, with a degree of ethoxylation of between 10 and 80, preferably 25 to 40, such as, for example, the Emulsogen®EL series (Clariant) or Agnique®CSO series (Cognis),
5) polyalkoxylated, preferably polyethoxylated, sorbitan esters, such as, for example, Atplus®309 F (Uniqema) or Alkamuls® series (Rhodia)
6) di- and tri-block copolymers, for example of alkylene oxides, for example ethylene oxide and propylene oxide with mean molar masses of between 200 and 10 000, preferably 1000 to 4000, g/mol, the mass fraction of the polyethoxylated block varying between 10 and 80%, such as, for example, the Genapol®PF series (Clariant), Pluronic® series (BASF), or Synperonic®PE series (Uniqema).

Preferred nonionic emulsifiers and dispersants are, for example, polyethoxylated alcohols, polyethoxylated triglycerides which contain hydroxy-fatty acids, and polyethylene oxide/polypropylene oxide block copolymers.

Ionic emulsifiers and dispersants are also suitable, for example:
1) polyalkoxylated, preferably polyethoxylated, emulsifiers/dispersants (cf. component e) which are ionically modified, for example by reaction of the terminal free hydroxyl function of the polyethylene oxide block to give a sulfate ester or phosphate ester (for example as alkali and alkaline earth metal salts), such as, for example, Genapol®LRO or Dispergiermittel 3618 (Clariant), Emulphor® (BASF) or Crafol®AP (Cognis),
2) alkali and alkaline earth metal salts of alkylarylsulfonic acids with linear or branched alkyl chain, such as Phenylsulfonat CA or Phenylsulfonat CAL (Clariant), Atlox® 3377BM (ICI), Empiphos®TM series (Huntsman)
3) Polyelectrolytes such as lignosulfonates and Kraft lignosulfonates, condensates of naphthalenesulfonate and formaldehyde, polystyrene sulfonate or sulfonated unsaturated or aromatic polymers (polystyrenes, polybutadienes or polyterpenes), such as the Tamol® series (BASF), Morwet®D425 (Witco), Kraftsperse® series (Westvaco), Borresperse® series (Borregard).

Preferred ionic emulsifiers/dispersants are polyacrylates and lignosulfonates, for example from Mead Westvaco (Reax® 88B) or Borregard (Borresperse® NA). The content of the surfactants b) in the solid formulations according to the invention preferably amounts to 0.1 to 30% by weight, especially preferably 5 to 25% by weight.

The content of water c) of the solid formulations can be adjusted for example by adding water in the required amount to the mixture, for example by spraying water onto granules, powders or dusts, or by removing water which had been added in excess in a controlled manner, for example by spray-drying, so that the water content does not fall short of 2% by weight.

A preferred variant of an embodiment is that the water content in the solid formulation amounts to at least 2.5% by weight. Especially preferred are solid formulations in which the water content amounts to from 2 to 10% by weight, in particular from 2.5 to 10% by weight and very especially preferably from 2.5 to 5% by weight.

Suitable optional agrochemical active substances d) which are other than component a) are, for example, insecticides, acaricides, herbicides, fungicides, safeners, fertilizers such as ammonium sulfate, ammonium hydrogen sulfate, urea or mixtures thereof, and/or growth regulators.

Suitable agrochemical active substances d) other than component a) which are present in the solid formulations according to the invention are, for example, safeners which are capable of reducing or avoiding damage to the crop plant. Suitable safeners are known, for example, from WO-A-96/14747 and the literature cited therein.

Examples of suitable safeners are the following groups of compounds:
1) compounds of the dichlorophenylpyrazoline-3-carboxylic acid (S1) type, preferably compounds such as ethyl 1-(2,4-dichlorophenyl)-5-(ethoxy-carbonyl)-5-methyl-2-pyrazoline-3-carboxylate (S1-1, mefenpyr-diethyl, PM p. 781-782) and related compounds as are described in WO 91/07874,
2) dichlorophenylpyrazolecarboxylic acid derivatives, preferably compounds such as ethyl 1-(2,4-dichlorophenyl)-5-methylpyrazole-3-carboxylate (S1-2), ethyl 1-(2,4-dichlorophenyl)-5-isopropylpyrazole-3-carboxylate (S1-3), ethyl 1-(2,4-dichlorophenyl)-5-(1,1-dimethylethyl)pyrazole-3-carboxylate (S1-4), ethyl 1-(2,4-dichlorophenyl)-5-phenylpyrazole-3-carboxylate (S1-5) and related compounds as are described in EP-A-0 333 131 and EP-A-0 269 806.
3) compounds of the triazolecarboxylic acid (S1) type, preferably compounds such as fenchlorazol, viz. ethyl 1-(2,4-dichlorophenyl)-5-trichloromethyl-(1H)-1,2,4-triazole-3-carboxylate (S1-6, fenchlorazole-ethyl, PM p. 385-386) and related compounds (see EP-A-0 174 562 and EP-A-0 346 620);
4) compounds of the 5-benzyl- or 5-phenyl-2-isoxazoline-3-carboxylic acid type, or of the 5,5-diphenyl-2-isoxaline-3-carboxylic acid type preferably compounds such as ethyl 5-(2,4-dichlorobenzyl)-2-isoxazoline-3-carboxylate (S1-7) or ethyl 5-phenyl-2-isoxazoline-3-carboxylate (S1-8), and related compounds as are described in WO 91/08202, or ethyl 5,5-diphenyl-2-isoxazolinecarboxylate (S1-9, isoxadifen-ethyl) or -n-propyl 5,5-diphenyl-2-isoxazolinecarboxylate (S1-10) or ethyl 5-(4-fluorophenyl)-5-phenyl-2-isoxazoline-3-carboxylate (S1-11), as they are described in the patent application (WO-A-95/07897),
5) compounds of the 8-quinolinoxyacetic acid (S2) type, preferably
1-methylhex-1-yl (5-chloro-8-quinolinoxy)acetate (S2-1; cloquintocet-mexyl, PM p. 263-264),
1,3-dimethylbut-1-yl (5-chloro-8-quinolinoxy)acetate (S2-2),
4-allyloxybutyl(5-chloro-8-quinolinoxy)acetate (S2-3),
1-allyloxyprop-2-yl (5-chloro-8-quinolinoxy)acetate (S2-4),
ethyl (5-chloro-8-quinolinoxy)acetate (S2-5),
methyl (5-chloro-8-quinolinoxy)acetate (S2-6),
allyl (5-chloro-8-quinolinoxy)acetate (S2-7),
2-(2-propylideneiminoxy)-1-ethyl (5-chloro-8-quinolinoxy)acetate (S2-8),
2-oxoprop-1-yl (5-chloro-8-quinolinoxy)acetate (S2-9)
and related compounds as are described in EP-A-86 750, EP-A-94 349 and EP-A-191 736 or EP-A-0 492 366.
6) compounds of the (5-chloro-8-quinolinoxy)malonic acid type, preferably compounds such as diethyl (5-chloro-8-quinolinoxy)malonate, diallyl (5-chloro-8-quinolinoxy)malonate, methyl ethyl (5-chloro-8-quinolinoxy)malonate and related compounds as are described in EP-A-0 582 198.
7) active substances of the type of the phenoxyacetic acid derivatives or phenoxypropionic acid derivatives or of the aromatic carboxylic acids such as, for example, 2,4-dichlorophenoxyacetic acid (and esters) (2,4-D), 4-chloro-2-methylphenoxypropionic ester (mecoprop), MCPA or 3,6-dichloro-2-methoxybenzoic acid (and esters) (dicamba).
8) active substances of the pyrimidine type, such as "fenclorim" (PM, p. 512-511) (=4,6-dichloro-2-phenylpyrimidine),
9) active substances of the dichloroacetamide type, which are frequently employed as pre-emergence safener (soil-acting safeners), such as, for example,
"dichlormid" (PM, p. 363-364) (=N,N-diallyl-2,2-dichloroacetamide),
"R-29148" (=3-dichloroacetyl-2,2,5-trimethyl-1,3-oxazolidone from Stauffer),
"benoxacor" (PM, p. 102-103) (=4-dichloroacetyl-3,4-dihydro-3-methyl-2H-1,4-benzoxazine).

"PPG-1292" (=N-allyl-N[(1,3-dioxolan-2-yl)methyl] dichloroacetamide from PPG Industries),
"DK-24" (=N-allyl-N-[(allylaminocarbonyl)methyl] dichloroacetamide from Sagro-Chem),
"AD-67" or "MON 4660" (=3-dichloroacetyl-1-oxa-3-azaspiro[4,5]decane from Nitrokemia or Monsanto),
"dicyclonon" or "BAS145138" or "LAB145138" (=3-dichloroacetyl-2,5,5-trimethyl-1,3-diazabicyclo[4.3.0]nonane from BASF) and
"furilazol" or "MON 13900" (see PM, 637-638) (=(RS)-3-dichloroacetyl-5-(2-furyl)-2,2-dimethyloxazolidone)
10) active substances of the dichloroacetone derivative type, such as, for example,
"MG 191" (CAS-Reg. No. 96420-72-3) (=2-dichloromethyl-2-methyl-1,3-dioxolane from Nitrokemia),
11) active substances of the oxyimino compound type, which are known as seed-dressing agents, such as, for example,
"oxabetrinil" (PM, p. 902-903) (=(Z)-1,3-dioxolan-2-ylmethoxyimino(phenyl)-acetonitrile), which is suitable as seed-dressing safener against damage caused by metolachlor,
"fluxofenim" (PM, p. 613-614) (=1-(4-chlorophenyl)-2,2,2-trifluoro-1-ethanone O-(1,3-dioxolan-2-ylmethyl) oxime, which is known as seed-dressing safener against damage caused by metolachlor, and
"cyometrinil" or "CGA-43089" (PM, p. 1304) (=(Z)-cyanomethoxyimino-(phenyl)acetonitrile), which is known as seed-dressing safener against damage caused by metolachlor,
12) active substances of the thiazolecarboxylic ester type, which are known as seed-dressing agents, such as, for example,
"flurazol" (PM, p. 590-591) (=benzyl 2-chloro-4-trifluoromethyl-1,3-thiazole-5-carboxylate), which is known as seed-dressing safener against damage caused by alachlor and metolachlor,
13) active substances of the naphthalenedicarboxylic acid derivative type, which are known as seed-dressing agents, such as, for example,
"naphthalic anhydride" (PM, p. 1342) (=1,8-naphthalenedicarboxylic anhydride), which is known as seed-dressing safener for maize against damage caused by thiocarbamate herbicides,
14) active substances of the chromanacetic acid derivative type, such as, for example,
"CL 304415" (CAS Reg. No. 31541-57-8) (=2-84-carboxychroman-4-yl)-acetic acid from American Cyanamid),
15) active substances which, in addition to herbicidal activity against harmful plants, also exhibit a safener effect on crop plants, such as, for example,
"dimepiperate" or "MY-93" (PM, p. 404-405) (=S-1-methyl-1-phenylethyl piperidine-1-thiocarboxylate),
"daimuron" or "SK 23" (PM, p. 330) (=1-(1-methyl-1-phenylethyl)-3-p-tolyl-urea),
"cumyluron"="JC-940" (=3-(2-chlorophenylmethyl)-1-(1-methyl-1-phenyl-ethyl)urea, see JP-A-60087254),
"methoxyphenon" or "NK 049" (=3,3'-dimethyl-4-methoxybenzophenone),
"CSB" (=1-bromo-4-(chloromethylsulfonyl)benzene) (CAS Reg. No. 54091-06-4 from Kumiai),
Compounds of the acylsulfamoylbenzamide type, for example of the following formula (VIII), which are known, for example, from WO 99/16744.

(VIII) structure shown with $R^{21}$ and $R^{22}$ substituents on an acylsulfamoylbenzamide scaffold.

| Compound No. | $R^{21}$ | $R^{22}$ |
|---|---|---|
| S3-1 | cyclopropyl | 2-OCH$_3$ |
| S3-2 | cyclopropyl | 2-OCH$_3$, 5-Cl |
| S3-3 | ethyl | 2-OCH$_3$ |
| S3-4 | isopropyl | 2-OCH$_3$, 5-Cl |
| S3-5 | isopropyl | 2-OCH$_3$ |

Preferred safeners are mefenpyr, fenchlorazol, isoxadifen, cloquintocet and their $C_1$-$C_{10}$-alkyl esters, in particular mefenpyr-diethyl (S1-1), fenchlorazol-ethyl (S1-6), isoxadifen-ethyl (S1-9), cloquintocet-mexyl (S2-1), and (S3-1).

Suitable agrochemical active substances other than component a) which can optionally be present as component d) in the solid formulations according to the invention are preferably herbicidal active substances, for example:
A) Herbicides of the phenoxyphenoxy- and heteroaryloxyphenoxycarboxylic acid derivatives type, such as
A1) Phenoxyphenoxy- and benzyloxyphenoxycarboxylic acid derivatives, for example methyl 2-(4-(2,4-dichlorophenoxy)phenoxy)propionate (diclofop-methyl),
methyl 2-(4-(4-bromo-2-chlorophenoxy)phenoxy)propionate (DE-A 26 01 548),
methyl 2-(4-(4-bromo-2-fluorophenoxy)phenoxy)propionate (U.S. Pat. No. 4,808,750),
methyl 2-(4-(2-chloro-4-trifluoromethylphenoxy)phenoxy)propionate (DE-A 24 33 067),
methyl 2-(4-(2-fluoro-4-trifluoromethylphenoxy)phenoxy)propionate (U.S. Pat. No. 4,808,750),
methyl 2-(4-(2,4-dichlorobenzyl)phenoxy)propionate (DE-A 24 17 487),
ethyl 4-(4-(4-trifluoromethylphenoxy)phenoxy)pent-2-enoate,
methyl 2-(4-(4-trifluoromethylphenoxy)phenoxy)propionate (DE-A 24 33 067);
A2) "Mononuclear" heteroaryloxyphenoxyalkanecarboxylic acid derivatives, for example
ethyl 2-(4-(3,5-dichloropyridyl-2-oxy)phenoxy)propionate (EP-A 0 002 925),
propargyl 2-(4-(3,5-dichloropyridyl-2-oxy)phenoxy)propionate (EP-A 0 003 114),
methyl 2-(4-(3-chloro-5-trifluoromethyl-2-pyridyloxy)phenoxy)propionate (EP-A 0 003 890),
ethyl 2-(4-(3-chloro-5-trifluoromethyl-2-pyridyloxy)phenoxy)propionate (EP-A 0 003 890),
propargyl 2-(4-(5-chloro-3-fluoro-2-pyridyloxy)phenoxy)propionate (EP-A 0 191 736),
butyl 2-(4-(5-trifluoromethyl-2-pyridyloxy)phenoxy)propionate
(fluazifop-butyl);
A3) "Binuclear" heteroaryloxyphenoxyalkanecarboxylic acid derivatives, for example
methyl and ethyl 2-(4-(6-chloro-2-quinoxalyloxy)phenoxy)propionate (quizalofopmethyl and quizalofopethyl),
methyl 2-(4-(6-fluoro-2-quinoxalyloxy)phenoxy)propionate (see J. Pest. Sci. Vol. 10, 61 (1985)),
2-isopropylideneaminooxyethyl 2-(4-(6-chloro-2-quinoxalyloxy)phenoxy)propionate (propaquizafop), ethyl 2-(4-(6-chlorobenzoxazol-2-yloxy)phenoxy)propionate (fenoxaprop-ethyl), its D(+) isomer (fenoxaprop-P-ethyl, EX) and ethyl 2-(4-(6-chlorobenzthiazol-2-yloxy)phenoxy)propionate (DE-A 26 40 730),
tetrahydro-2-furylmethyl 2-(4-(6-chloroquinoxalyloxy)phenoxy)propionate (EP-A 0 323 727);
B) Chloroacetanilides, for example
N-methoxymethyl-2,6-diethylchloroacetanilide (alachlor),
N-(3-methoxyprop-2-yl)-2-methyl-6-ethylchloroacetanilide (metolachlor),
2,6-dimethyl-N-(3-methyl-1,2,4-oxadiazol-5-ylmethyl) chloroacetanilide,
N-(2,6-dimethylphenyl)-N-(1-pyrazolylmethyl)chloroacetamide (metazachlor);
C) Thiocarbamates, for example
S-ethyl N,N-dipropylthiocarbamate (EPTC),
S-ethyl N, N-diisobutylthiocarbamate (butylate);
D) Cyclohexanedione oximes, for example
methyl 3-(1-allyloxyiminobutyl)-4-hydroxy-6,6-dimethyl-2-oxocyclohex-3-enecarboxylate (alloxydim),
2-(1-ethoxyiminobutyl)-5-(2-ethylthiopropyl)-3-hydroxycyclohex-2-en-1-one (sethoxydim),
2-(1-ethoxyiminobutyl)-5-(2-phenylthiopropyl)-3-hydroxycyclohex-2-en-1-one (cloproxydim),
2-(1-(3-chloroallyloxy)iminobutyl)-5-(2-ethylthiopropyl)-3-hydroxycyclohex-2-en-1-one,
2-(1-(3-chloroallyloxy)iminopropyl)-5-(2-ethylthiopropyl)-3-hydroxycyclohex-2-en-1-one (clethodim),
2-(1-ethoxyiminobutyl)-3-hydroxy-5-(thian-3-yl)cyclohex-2-enone (cycloxydim),
2-(1-ethoxyiminopropyl)-5-(2,4,6-trimethylphenyl)-3-hydroxycyclohex-2-en-1-one (tralkoxydim);
E) Benzoylcyclohexanediones, for example
2-(2-chloro-4-methylsulfonylbenzoyl)cyclohexane-1,3-dione (SC-005 1, E P-A 0 137 963), 2-(2-nitrobenzoyl)-4,4-dimethylcyclohexane-1,3-dione (EP-A 0 274 634),
2-(2-nitro-4-methylsulfonylbenzoyl)-4,4-dimethylcyclohexane-1,3-dione (WO 91/13548, mesotrione);
F) S—(N-Aryl-N-alkylcarbamoylmethyl)dithiophosphonates such as S—[N-(4-chlorophenyl)-N-isopropylcarbamoylmethyl]O,O-dimethyl dithiophosphate (anilophos).
G) Alkylazines, for example as described in WO-A 97/08156, WO-A-97/31904, DE-A-1 9826670, WO-A-98/15536, WO-A-8/15537, WO-A-98/15538, WO-A-98/15539 and also DE-A-1 9828519, WO-A-98/34925, WO-A-98/42684, WO-A-99/18100, WO-A-99/19309, WO-A-99/37627 and WO-A-99/65882, preferably those of the formula (G)

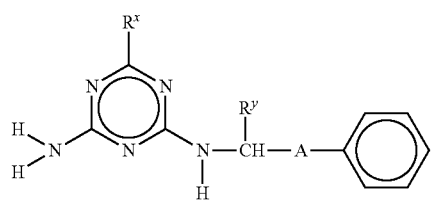

in which
$R^x$ is $(C_1-C_4)$-alkyl or $(C_1-C_4)$-haloalkyl;
$R^y$ is $(C_1-C_4)$-alkyl, $(C_3-C_6)$-cycloalkyl or $(C_3-C_6)$-cycloalkyl-$(C_1-C_4)$-alkyl and A is —$CH_2$—, —$CH_2$—$CH_2$—, —$CH_2$—$CH_2$—$CH_2$—, —O—, —$CH_2$—$CH_2$—O—, —$CH_2$—$CH_2$—$CH_2$—O—, especially preferably those of the formula G1-G7

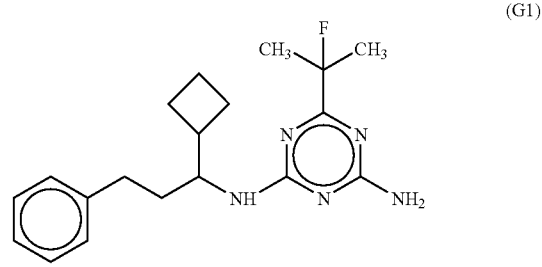

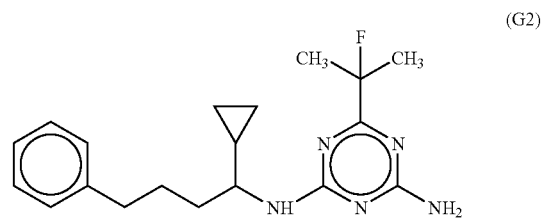

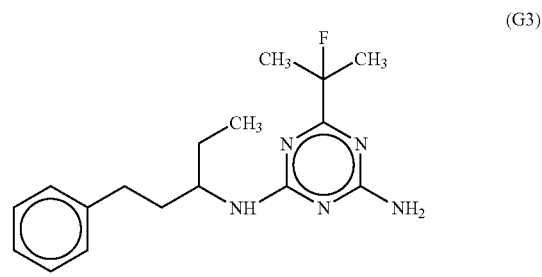

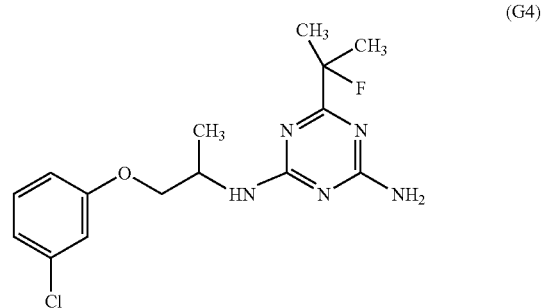

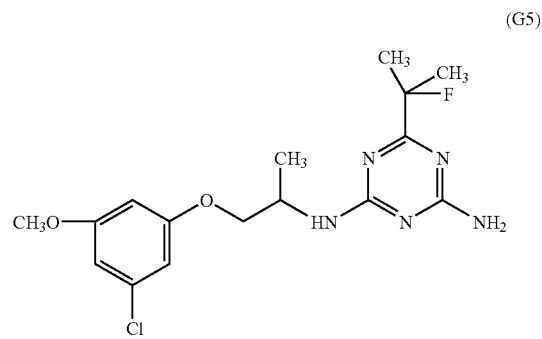

-continued

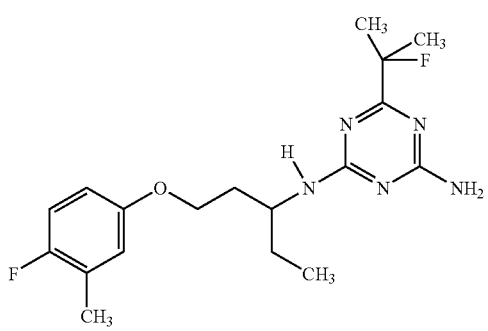

(G6)

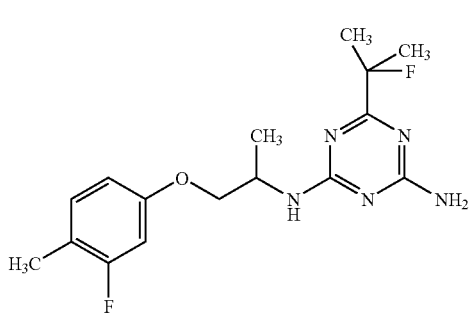

(G7)

H) Phosphorus-containing herbicides, for example of the glusosinate type, such as glufosinate in the narrow sense, i.e. D,L-2-amino-4-[hydroxy(methyl)phosphinyl]-butanoic acid, glufosinatemonoammonium salts, L-glufosinate, L- or (2S)-2-amino-4-[hydroxy(methyl)phosphinyl]butanoic acid, L-glufosinatemonoammonium salt or bialaphos (or bilanafos), i.e. L-2-amino-4-[hydroxy(methyl)phosphinyl]butanoyl-L-alanyl-L-alanine, in particular its sodium salt, or of the glyphosate type, such as glyphosate, i.e. N-(phosphonomethyl)glycine, glyphosatemonoisopropylammonium salt, glyphosate sodium salt, or sulfosate, i.e. N-(phosphonomethyl)glycine trimesium salt=N-(phosphonomethyl)glycine trimethyl-sulfoxonium salt.

The herbicides of groups A to H are known, for example, from each of the specifications stated above and from "The Pesticide Manual", 12$^{th}$ Edition, 2000, The British Crop Protection Council, "Agricultural Chemicals Book II—Herbicides—", by W. T. Thompson, Thompson Publications, Fresno Calif., USA 1990 and "Farm Chemicals Handbook '90", Meister Publishing Company, Willoughby Ohio, USA, 1990.

Agrochemical active substances d) other than component (a) which are optionally present and which are suitable for the solid formulations according to the invention are the known active substances mentioned hereinbelow as they are described for example in Weed Research 26, 441445 (1986), or "The Pesticide Manual", 12th edition, The British Crop Protection Council, 2000, and literature cited therein, for example in formulations of mixtures or as components in tank mixers. The compounds are given either with the common name of the International Organization for Standardization (ISO) or by the chemical name, if appropriate together with a conventional code number, and always comprise all use forms such as acids, salts, esters and isomers such as stereoisomers and optical isomers: acetochlor; acifluorfen; aclonifen; AKH 7088, i.e. [[[1-[5-[2-chloro-4-(trifluoromethyl)phenoxy]-2-nitrophenyl]-2-methoxyethylidene]amino]oxy]acetic acid and its methyl ester; alachlor; alloxydim; ametryn; amitrol; AMS, i.e. ammonium sulfamate; anilofos; asulam; atrazine; azafenidine (DPX-R6447), aziprotryn; barban; BAS 516 H, i.e. 5-fluoro-2-phenyl-4H-3,1-benzoxazin-4-one; benazolin; benfluralin; benfuresate; bensulide; bentazone; benzofluor; benzoylprop-ethyl; benzthiazuron; bialaphos; bifenox; bispyribac-sodium (KIH-2023), bromacil; bromobutide; bromofenoxim; bromoxynil, in particular bromoxynil-octanoate and bromoxynil-heptanoate; butachlor; butamifos; butenachlor; buthidazole; butralin; butroxydim (ICI-0500), butylate; cafenstrole (CH-900); carbetamide; cafentrazone; CDAA, i.e. 2-chloro-N,N-di-2-propenylacetamide; CDEC, i.e. 2-chloroallyl diethyldithiocarbamate; chlomethoxyfen; chloramben; cloransulam-methyl (XDE-565), chlorazifop-butyl, chlorbromuron; chlorbufam; chlorfenac; chlorflurenol-methyl; chloridazon; chlornitrofen; chlorotoluron; chloroxuron; chlorpropham; chlorthal-dimethyl; chlorthiamid; cinidon-ethyl, cinmethylin; clethodim; clodinafop and its ester derivatives (for example clodinafop-propargyl); clomazone; clomeprop; cloproxydim; clopyralid; cumyluron (JC 940); cyanazine; cycloate; cycloxydim; cycluron; cyhalofop and its ester derivatives (for example butyl ester, DEH-112); cyperquat; cyprazine; cyprazole; 2,4-D; 2,4-DB; dalapon; desmedipham; desmetryn; di-allate; dicamba; dichlobenil; dichlorprop; diclofop and its esters such as diclofop-methyl; diclosulam (XDE-564), diethatyl; difenoxuron; difenzoquat; diflufenican; diflufenzopyr-sodium (SAN-835H), dimefuron; dimethachlor; dimethametryn; dimethenamid (SAN-582H); dimidazone, methyl 5-(4,6-dimethylpyrimidin-2-yl-carbamoylsulfamoyl)-1-(2-pyridyl)-pyrazole-4-carboxylate (NC-330); triaziflam (IDH-1105), cinosulfon; dimethipin, dinitramine; dinoseb; dinoterb; diphenamid; dipropetryn; diquat; dithiopyr; diuron; DNOC; eglinazine-ethyl; EL 177, i.e. 5-cyano-1-(1,1-dimethylethyl)-N-methyl-1H-pyrazole-4-carboxamide; endothal; indanofan (MK-243), EPTC; esprocarb; ethalfluralin; ethidimuron; ethiozin; ethofumesate; F5231, i.e. N-[2-chloro-4-fluoro-5-[4-(3-fluoropropyl)-4,5-dihydro-5-oxo-1H-tetrazol-1-yl]phenyl]ethanesulfonamide; ethoxyfen and its esters (for example ethyl ester, HN-252); etobenzanid (HW 52); 3-(4-ethoxy-6-ethyl-1,3,5-triazin-2-yl)-1-(2,3-dihydro-1,1-dioxo-2-methylbenzo[b]-thiophene-7-sulfonyl)urea (EP-A 079 683); 3-(4-ethyl-6-methoxy-1,3,5-triazin-2-yl)-1-(2,3-dihydro-1,1-dioxo-2-methylbenzo[b]-thiophene-7-sulfonyl) urea (EP-A 079 683); fenoprop; clomazone, fenoxaprop and fenoxaprop-P and their esters, for example fenoxaprop-P-ethyl and fenoxaprop-ethyl; butroxydimfenuron; flampropmethyl; flufenacet (BAY-FOE-5043), fluazifop and fluazifop-P and their esters, for example fluazifop-butyl and fluazifop-P-butyl, florasulam (DE-570); fluchloralin; flumetsulam; fluometuron; flumiclorac and its esters (for example pentyl ester, S-23031); flumioxazin (S482); flumipropyn; flupoxam (KNW-739); fluorodifen; fluoroglycofen-ethyl; flupropacil (UBIC-4243); fluridone; flurochloridone; fluroxypyr; flurtamone; fluthiacet-methyl (KIH-9201), fomesafen; fosamine; furyloxyfen; glufosinate; glyphosate; halosafen; halosulfuron and its esters (for example methyl ester, NC-319); haloxyfop and its esters; haloxyfop-P (=R-haloxyfop) and its esters; hexazinone; imazamethabenz-methyl; imazamox (AC-299263), imazapyr; imazaquin and salts such as the ammonium salt; imazapic; imazethapyr; imazosulfuron; ioxynil; isocarbamid; isopropalin; isoproturon; isouron; isoxaben; isoxapyrifop; karbutilate; lactofen; lenacil; linuron; MCPA; MCPB; mecoprop; mefenacet; mefluidid; metamitron; metazachlor; methabenzthiazuron; metam; methazole; methoxyphenone; methyldymron; metobenzuron, mesosulfuron-methyl, mesosulfuron-methyl (WO 95/10507); metobromuron; metolachlor; S-metolachlor, metosulam (XRD 511); metoxuron; metribuzin; maleic hydrazide; molinate; monalide; monocarbamide dihydrogensulfate; monolinuron; monuron; MT 128, i.e. 6-chloro-N-(3-chloro-2-propenyl)-5-methyl-N-phenyl-3-pyridazineamine; MT 5950, i.e. N-[3-chloro-4-(1-methylethyl)phenyl]-2-methylpentanamide; foramsulfuron (WO 95/01344); naproanilide; napropamide; naptalam; NC 310, i.e. 4-(2,4-dichlorobenzoyl)-1-methyl-5-benzyloxypyrazole; neburon; nipyraclophen; nitralin; nitrofen; nitrofluorfen; norflurazon; orbencarb; oryzalin; oxadiargyl (RP-020630); oxadiazon; oxaziclomefone (MY-100), oxyfluorfen; paraquat; pebulate; pendimethalin; pentoxazone (KPP-314), perfluidone; phenisopham; phenmedipham; picloram; pinoxaden; piperophos; pyributicarb; pirifenop-butyl; pretilachlor; procyazine; prodiamine; profluralin; proglinazine-ethyl; prometon; prometryn; propachlor; propanil; propaquizafop and its esters; propazine; propham; propisochlor; propyzamide; prosulfalin; prosulfocarb; prynachlor; pyraflufen-ethyl (ET-751), chloridazon; pyrazoxyfen; pyribenzoxim, pyridate; pyriminobac-methyl (KIH-6127), pyrithiobac (KIH-2031); pyroxofop and its esters (for example propargyl ester); quinclorac; quinmerac; quizalofop, quizalofop and quizalofop-P and their ester derivatives, for example quizalofop-ethyl; quizalofop-P-tefuryl and -ethyl; S 275, i.e. 2-[4-chloro-2-fluoro-5-(2-propynyloxy)phenyl]-4,5,6,7-tetrahydro-2H-indazole; secbumeton; sethoxydim; siduron; simazine; simetryn; SN 106279, i.e. 2-[[7-[2-chloro-4-(trifluoromethyl)phenoxy]-2-naphthalenyl]oxy]propanoic acid and its methyl ester; flazasulfuron (FMC-97285, F-6285); sulfazuron; glyphosate-trimesium (ICI-A0224); TCA; tebutam (GCP-5544); tebuthiuron; tepraloxydim (BAS-620H), terbacil; terbucarb; terbuchlor; terbumeton; terbuthylazine; terbutryn; TFH 450, i.e. N,N-diethyl-3-[(2-ethyl-6-methylphenyl)sulfonyl]-1H-1,2,4-triazole-1-carboxamide; thenylchlor (NSK-850); thiazafluron; thiazopyr (Mon-13200); thidiazimin (SN-124085); thiobencarb; tiocarbazil; tralkoxydim; tri-allate; triazofenamide; triclopyr; tridiphane, trietazine; trifluralin; trimeturon; tsitodef; vernolate; WL 110547, i.e. 5-phenoxy-1-[3-(trifluoromethyl)phenyl]-1H-tetrazole; UBH-509; D489; LS 82-556; KPP-300; KPP-421, MT-146, NC-324; butenachlor (KH-218); DPX-N8189; haloxyfop-etotyl (DOWCO-535); DK-8910; flumioxazin (V-53482); PP-600; MBH-001, amicarbazone, aminopyralid, beflubutamid, benzobicyclon, benzofenap, benzfendizone, butafenacil, chlorfenprop, cloprop, daimuron, dichlorprop-P, dimepipeate, dimethenamid-P, fentrazamide, flamprop-M, fluazolate, indanofan, isoxachlortole, isoxaflutole, MCPA-thioethyl, mecoprop-P, mesotrione, metamifop, penoxsulam, pethoxamid, picolinafen, profluazol, profoxydim, pyraclonil, pyrazolynate, pyridafol, pyriftalid, sulcotrione, thidiazuron.

If the solid formulations according to the invention comprise agrochemical active substances d), they amount to 1 to 50% by weight, in particular 5 to 30% by weight.

The total active substance content (sum of components a)+d)) present in the solid formulations according to the invention is preferably between 26 and 97.9% by weight, in particular between 50 and 95% by weight.

Customary adjuvants and additives (component e)) which may additionally be present in the solid formulations according to the invention are, for example, thickeners and thixotropic agents, anti-drift agents, tackifiers, penetrants, preservatives, antifreeze agents, antioxidants, solubilizers, fillers, carriers and colorants, antifoams, evaporation inhibitors, and pH regulators and viscosity regulators. Preferred adjuvants and additives e) are tackifiers and carriers.

Tackifiers can be water-soluble or water-dispersible substances, for example polymers such as homopolymers or copolymers of vinyl-group-containing monomers. Examples are copolymers of vinylpyrrolidone and dimethylaminoethyl methacrylate, of vinyl chloride and vinyl acetate, of propenesulfonic acid and polyvinyl acetate, and partially hydrolyzed derivatives thereof, and optionally partially hydrolyzed polyvinyl acetates and polyvinylpyrrolidones. Preferred are water-soluble polymers such as partially hydrolyzed polyvinyl acetates or polyvinylpyrrolidones, especially preferred are polyvinylpyrrolidone brands of BASF (for example Luviskol® types such as Luviskol®D K 17, Luviskol® K 30, Luviskol® K 60, Luviskol® K 80, Luviskol® K 90) or International Specialty Products (for example Agrimer® types such as Agrimer® 15, Agrimer® 30, Agrimer® 60, Agrimer® 90, Agrimer® XL, Agrimer® XLF, Agrimer® AT, Agrimer® ATF).

Carriers can be for example water-soluble substances or substances which are not soluble in water but which can be ground to such a fineness that they are capable of forming an aqueous dispersion under suitable conditions. Preferred carriers are inorganic or organic carriers, for example natural and synthetic silicates, aluminum hydroxide, calcite, barium sulfate, and the carbonates, citrates, oxides, silicates, stearates, sulfates and phosphates of magnesium and/or calcium, polymeric, oligomeric and monomeric carbohydrates, for example starch or cellulose and their synthetic derivatives, crosslinked acrylamide/acrylic acid copolymers and their salts, crosslinked polyvinylpyrrolidones, and optionally partially hydrolyzed polyvinyl acetates. Preferred are monomeric or oligomeric carbohydrates, for example consisting of one or two sugar units, especially preferred are disaccharides such as maltose, sucrose and lactose.

If the solid formulations according to the invention comprise adjuvants and additives e), they amount to 0.1 to 50% by weight, preferably to 1 to 25% by weight.

Preferred are solid formulations according to the invention with a high concentration of sulfonamides a), comprising:
a) 50 to 95% by weight, preferably 60 to 80% by weight, of one or more herbicidally active substances from the group of the sulfonamides, preferably from the group of the heteroaryl- or phenylsulfonylaminocarbonyltriazolinones, in particular propoxycarbazone (A5.1) and its salts, such as the sodium salt (A5.2),
b) 5 to 30% by weight of one or more surfactants,
c) 2 to 10% by weight, preferably 2 to 5% by weight, of water,
d) optionally 1 to 50% by weight, preferably 5 to 30% by weight, of one or more agrochemical active substances other than a),
e) optionally 0.1 to 25% by weight of customary adjuvants and additives other than b), in particular adjuvants and carriers.

In an especially preferred embodiment, the solid formulation according to the invention comprises
a) 50 to 95% by weight, preferably 60 to 80% by weight, of one or more herbicidal active substances from the group of the heteroaryl- or phenylsulfonylaminocarbonyltriazolinones, in particular propoxycarbazone (A5.1) and its salts, such as the sodium salt (A5.2),
b1) 5 to 20% by weight of one or more dispersants, in particular water-soluble polymeric and anionic dispersants such as polyacrylates or lignosulfonates,
b2) 0.1 to 5% by weight of one or more wetters, in particular monomeric anionic wetters, such as mono- or dialkylnaphthalenesulfonic acid and its salts,
c) 2 to 5% by weight of water,
d) optionally 1 to 50% by weight of one or more herbicides or safeners other than a), e1) 0.1 to 25% by weight of one or more tackifiers, preferably water-soluble, polymeric and nonionic tackifiers such as polyvinylpyrrolidones, e2) 0.1 to 25% by weight of one or more carriers, preferably monomeric or oligomeric carbohydrates such as disaccharides.

In one preferred variant embodiment, the solid formulations according to the invention are granules which are soluble in water and which are prepared by spray drying, in particular by spraying in a fluidized bed. The preferred granules have a particle size of $d_{10} \leqq 250$ µm, preferably $\leqq 220$ µm, $d_{50} \leqq 350$ µm, preferably $\leqq 310$ µm, and $d_{90} \leqq 450$ µm, preferably $\leqq 420$ µm.

For use, the solid formulations according to the invention can be applied in solid form or, if appropriate, converted into liquid formulations in the customary manner, for example by means of water, such as suspensions, emulsions, suspoemulsions or solutions. It can be advantageous to add further agrochemical active substances (for example components of tank mixers in the form of suitable formulations) and/or adjuvants and additives conventionally used for application purposes, for example autoemulsifying oils such as vegetable oils or liquid paraffins and/or fertilizers to the resulting spray mixtures. The present invention therefore also relates to those herbicidal compositions obtainable from the solid formulations according to the invention, for example by dissolving or dispersing in water. All of the abovementioned solid and liquid formulations are hereinbelow referred to as herbicidal compositions.

The herbicidal compositions according to the invention have an outstanding herbicidal activity against a broad spectrum of economically important monocotyledonous and dicotyledonous harmful plants. The active ingredients also act efficiently on perennial weeds which produce shoots from rhizomes, rootstocks or other perennial organs and which are difficult to control. In this context, the compositions can be applied before sowing, pre-emergence or post-emergence, for example. Specific examples may be mentioned of some representatives of the monocotyledonous and dicotyledonous weed flora which can be controlled by the herbicidal compositions according to the invention, without the enumeration being a restriction to certain species.

Examples of weed species on which the herbicidal compositions act efficiently are, from amongst the monocotyledonous weed species *Apera spica venti, Avena* spp., *Alopecurus* spp., *Brachiaria* spp., *Digitaria* spp., *Lolium* spp., *Echinochloa* spp., *Panicum* spp., *Phalaris* spp., *Poa* spp., *Setaria* spp. and *Bromus* spp. such as *Bromus catharticus, Bromus secalinus, Bromus erectus, Bromus tectorum* and *Bromus japonicus* and *Cyperus* species from the annual group, and, among the perennial species *Agropyron, Cynodon, Imperata* and *Sorghum* and also perennial *Cyperus* species.

In the case of the dicotyledonous weed species, the spectrum of action extends to species such as, for example, *Abutilon* spp., *Amaranthus* spp., *Chenopodium* spp., *Chrysanthemum* spp., *Galium* spp. such as *Galium aparine, Ipomoea* spp., *Kochia* spp., *Lamium* spp., *Matricaria* spp., *Pharbitis* spp., *Polygonum* spp., *Sida* spp., *Sinapis* spp., *Solanum* spp., *Stellaria* spp., *Veronica* spp. and *Viola* spp., *Xanthium* spp., amongst the annuals, and *Convolvulus, Cirsium, Rumex* and *Artemisia* in the case of the perennial weeds.

The compositions according to the invention also act outstandingly efficiently on harmful plants which are found under the specific cultures in rice, such as, for example, *Echinochloa, Sagittaria, Alisma, Eleocharis, Scirpus* and *Cyperus*.

If the herbicidal compositions according to the invention are applied to the soil surface before germination, the weed seedlings are either prevented completely from emerging or else the weeds grow until they have reached the cotyledon stage, but then their growth stops, and, eventually, after three to four weeks have elapsed, they die completely.

If the herbicidal compositions according to the invention are applied post-emergence to the green parts of the plants, growth likewise stops drastically a very short time after the treatment, and the weed plants remain at the growth stage of the time of application, or they die completely after a certain time, so that in this manner competition by the weeds, which is harmful to the crop plants, is eliminated very early and in a sustained manner.

The herbicidal compositions according to the invention are distinguished by a rapid onset and a prolonged herbicidal activity. The rainfastness of the active substances in the combinations according to the invention is, as a rule, favorable. A particular advantage is that the dosage rates used in the herbicidal compositions, and the effective doses, of herbicidal compounds can be adjusted to such a low level that their soil activity is optimally low. This not only makes their use in sensitive crops possible in the first place, but contaminations of the groundwater are virtually avoided. The combination according to the invention of active substances makes possible a considerable reduction of the necessary application rate of the active substances.

The abovementioned properties and advantages are of use in practical weed control in order to keep agricultural crops free from undesired competitor plants and for safeguarding and/or increasing the quality and quantity of the yields. These novel compositions markedly outperform the technical standard with regard to the described properties.

Even though the herbicidal compositions according to the invention have an outstanding herbicidal activity against monocotyledonous and dicotyledonous weeds, crop plants of economically important crops such as dicotyledonous crops such as, for example, soybeans, cotton, oilseed rape, sugarbeet, or graminaceous crops such as wheat, barley, rye, oats, sorghum/millet, rice or maize, are harmed only to a minor extent, if at all. For these reasons, the present compounds are highly suitable for the selective control of undesired vegetation in stands of agriculturally useful plants or of ornamentals.

In addition, the herbicidal compositions according to the invention have outstanding growth-regulatory properties in crop plants. They engage in the plants' metabolism in a regulatory fashion and can thus be used for the directed control of plant constituents and for facilitating harvesting, such as, for example, by triggering desiccation and stunted growth. Moreover, they are also suitable for generally controlling and inhibiting undesired vegetative growth without destroying the plants in the process. Inhibition of the vegetative growth plays an important role in many monocotyledonous and dicotyledonous crops since lodging can be reduced, or prevented completely, thereby.

Owing to their herbicidal and plant-growth regulatory properties, the herbicidal compositions according to the invention can also be employed for controlling harmful plants in crops of genetically modified plants which are known or yet to be developed. As a rule, the transgenic plants are distinguished by particular advantageous properties, for example by resistances to certain pesticides, especially certain herbicides, resistances to plant diseases or to plant pathogens such as certain insects or microorganisms such as fungi, bacteria or viruses. Other particular properties concern for example the harvested material with regard to quantity, quality, storability, composition and specific constituents. Thus, transgenic plants with an increased starch content or with a modified starch quality or with a different fatty acid composition of the harvested material are known.

The use of the compositions according to the invention in economically important transgenic crops of useful plants and ornamentals, such as graminaceous crops such as wheat, barley, rye, oats, sorghum/millet, rice and maize or else crops of sugarbeet, cotton, soybean, oilseed rape, potato, tomato, pea and other vegetables is preferred. The compositions according to the invention may preferably be employed as herbicides in crops of useful plants which are resistant to the phytotoxic effects of the herbicides or which have been rendered resistant to the phytotoxic effects of the herbicides by recombinant means.

When the herbicidal compositions according to the invention are used in transgenic crops, effects are frequently observed—in addition to the effects on harmful plants which can be observed in other crops—which are specific for the application in the transgenic crop in question, for example a modified or specifically extended weed spectrum which can be controlled, modified application rates which can be employed for application, preferably good combining properties with the herbicides to which the transgenic crop is resistant, and an effect on growth and yield of the transgenic crop plants.

The present invention furthermore also relates to a method for controlling undesired vegetation, preferably in crops such as cereals (for example wheat, barley, rye, oats, rice, maize, sorghum/millet), sugarbeet, sugar cane, oilseed rape, cotton and soybean, especially preferably in monocotyledonous crops such as cereals, for example wheat, barley, rye, oats, their hybrids such as triticale, rice, maize and sorghum/millet, where one or more herbicidal compositions according to the invention are applied to the harmful plants, plant parts, plant seeds or the area on which the plants grow, for example the area under cultivation.

The crops can also be genetically modified or have been obtained by mutation selection and are preferably tolerant to acetolactate synthase (ALS) inhibitors.

The solid formulation of the present invention is distinguished by an outstanding chemical stability during preparation and storage. Moreover, the solid formulation is distinguished by an outstanding physical stability, good application characteristics and userfriendliness, and a high biological efficacy and selectivity.

EXAMPLES

1. Preparation of a Solid Formulation

The preparation is accomplished by dissolving or dispersing in water the constituents other than water in the amounts stated in Tables 1 and 2. The constituents b1), b2), e1), e2) correspond to the components b1), b2), e1), e2) mentioned as being preferred in the description. The resulting mixture comprises 20 to 80% by weight of water. To achieve the water content of at least 2% by weight, the drying time required with given process and plant parameters is then determined in a manner with which the skilled worker is familiar by establishing a drying curve. Using a commercially available fluidized-bed granulator, the mixture is subsequently converted into water-soluble granules at the drying time which has been determined beforehand.

TABLE 1

| | | Comparative example: A<br>% by weight |
|---|---|---|
| a) | Propoxycarbazone-sodium | 71.43 |
| b1) | Dispersant | 14.63 |
| b2) | Wetter | 0.24 |
| c) | Water | 0.73 |
| e1) | Carrier | 8.09 |
| e2) | Tackifier | 4.88 |

TABLE 2

| | | Examples according to the invention: | |
|---|---|---|---|
| | | B<br>% by weight | C<br>% by weight |
| a) | Propoxycarbazone-sodium | 71.43 | 71.43 |
| b1) | Dispersant | 14.61 | 14.30 |
| b2) | Wetter | 0.24 | 0.24 |
| c) | Water | 2.70 | 4.90 |
| e1) | Carrier | 6.15 | 4.36 |
| e2) | Tackifier | 4.87 | 4.77 |

2. Application Test 200 g of the granules prepared in accordance with example 1 are swiftly introduced into 500 ml of water with a temperature of 18° C. and a water hardness of 342 ppm, and the mixture is stirred for 10 seconds using a wooden stick. The mixture is left to act for 50 seconds, stirred for a further 10 seconds and then poured instantly onto a 300 μm screen of 10 cm diameter (residue 1). The mixture is allowed to run through the screen and then rinsed with 500 ml of water without pressure (residue 2). The remaining screen residues are observed with regard to the applicability of the granules in question. The results are compiled in Table 3 hereinbelow.

TABLE 3

| | Residue 1 | Residue 2 |
|---|---|---|
| Comparative example (1A) | Thick pasty coating | Coating does not dissolve and forms large agglomerates (whose inside is not wetted) |
| Example (1B) according to the invention | Uniform thin coating | Coating dissolves |
| Example (1C) according to the invention | Uniform thin coating | Coating dissolves |

It can be seen that the granules with a low water content (comparative example, Table 1) tend to clog the sieve and to form agglomerates, which is disadvantageous for application purposes, in particular when washing-in locks are used. In contrast, the granules according to the invention can be applied without any problems.

3. Emptying Test

A COEX plastic bottle (material: polyethylene/polyamide) is filled with the granules prepared in example 1 (A, B and C). Thereafter, the granules are emptied in order to make a slurry in water. Upon emptying the granules prepared in example 1A (comparative example), significant amounts remain in the plastic bottle, and dust is generated in large quantities. In contrast, the plastic bottles with the granules prepared in accordance with examples 1B and 1C (examples according to the invention) can be emptied completely, and no dusting can be observed.

We claim:

1. A solid formulation comprising
   a) 50 to 95% by weight of propoxycarbazone and/or its salts,
   b) 5 to 20% by weight of one or more dispersants,
   c) 0.1 to 5% by weight of one or more wetting agents,
   d) 0.1 to 25% by weight of one or more tackifiers,
   e) 0.1 to 25% by weight of one or more carriers, and
   f) 2 to 10% by weight of water.

2. The solid formulation as claimed in claim 1, which comprises, as component a), propoxycarbazone-sodium.

3. The solid formulation as claimed in claim 1, which comprises, as component b), lignin sulfonate.

4. The solid formulation as claimed in claim 1, which comprises, as component f), 2.5 to 5% by weight of water.

5. The solid formulation as claimed in claim 1, which further comprises, one or more agrochemical active substances other than a).

6. The solid formulation as claimed in claim 1, which comprises, as component c) an alkyl sulfate or alkyl naphthalinsulfonate.

7. The solid formulation as claimed in claim 1 in the form of a powder, a dust or of granules.

8. A method of controlling harmful plants, comprising the step of applying an effective amount of a solid formulation as claimed in claim 1 to the harmful plants, parts of the plants, plant seeds, or area on which the plants grow.

9. A method for preparing a herbicidal composition, comprising a step of combining a solid formulation as claimed in claim 1 with at least one additional solid or liquid substance.

10. The method as claimed in claim 9, wherein the herbicidal composition is a suspension, emulsion, suspoemulsion or a solution.

11. The solid formulation as claimed in claim 1, which comprises, as component d), polyvinylpyrrolidone or crosslinked polyvinylpyrrolidone.

12. The solid formulation as claimed in claim 1 in the form of water-soluble granules.

13. A method according to claim 9, wherein the at least one additional solid or liquid substance is a solid carrier and the herbicidal composition is in the form of solid granules.

14. The solid formulation as claimed in claim 1, which comprises, as component e), a natural or synthetic silicate or a disaccharide.

15. A process for the preparation of a solid formulation comprising
   a) 50 to 95% by weight of propoxycarbazone and/or its salts,
   b) 5 to 20% by weight of one or more dispersants,
   c) 0.1 to 5% by weight of one or more wetting agents,
   d) 0.1 to 25% by weight of one or more tackifiers,
   e) 0.1 to 25% by weight of one or more carriers, and
   f) 2 to 10% by weight of water,
   where (1) the components a)-e) are mixed and subsequently at least 2 to 10% by weight of water is added, or (2) the components a)-e) are mixed with an excess of water and the excess water is subsequently removed in such a way that the water content of the formulation is from 2 to 10% by weight.

* * * * *